United States Patent
Schweighardt et al.

(10) Patent No.: US 7,481,095 B2
(45) Date of Patent: Jan. 27, 2009

(54) LIQUID PARTICLE MASS MEASUREMENT IN GAS STREAMS

(75) Inventors: Frank Kenneth Schweighardt, Allentown, PA (US); David Hon Sing Ying, Allentown, PA (US); Dean Anthony Chin-Fatt, Schnecksville, PA (US); Kevin Boyle Fogash, Wescosville, PA (US); Charles Randall Kayhart, Alburtis, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 210 days.

(21) Appl. No.: 11/494,403

(22) Filed: Jul. 27, 2006

(65) Prior Publication Data

US 2007/0086008 A1 Apr. 19, 2007

Related U.S. Application Data

(63) Continuation-in-part of application No. 11/249,206, filed on Oct. 13, 2005, now Pat. No. 7,343,781.

(51) Int. Cl.
*G01N 21/00* (2006.01)
(52) U.S. Cl. ................................... 73/28.01
(58) Field of Classification Search ............... 73/28.01, 73/31.01, 31.02, 31.03; 356/337
See application file for complete search history.

(56) References Cited

U.S. PATENT DOCUMENTS

| 5,027,642 | A | | 7/1991 | Wen et al. |
| 5,305,630 | A | * | 4/1994 | Molozay et al. ............... 73/1.05 |
| 5,369,981 | A | | 12/1994 | Merz et al. |
| 5,587,519 | A | * | 12/1996 | Ronge et al. ................. 73/1.05 |
| 5,642,193 | A | | 6/1997 | Girvin et al. |
| 5,864,399 | A | | 1/1999 | Girvin et al. |
| 5,932,795 | A | | 8/1999 | Koutrakis et al. |
| 6,709,478 | B2 | | 3/2004 | Schlaps |
| 2006/0174941 | A1 | * | 8/2006 | Cohen et al. ................... 137/93 |

FOREIGN PATENT DOCUMENTS

DE 101 62 278 A1 7/2003

OTHER PUBLICATIONS

Ensuring the Purity of CO2 and Other Process Gases; Thermo Andersen brochures Apr. 2002.

* cited by examiner

*Primary Examiner*—Daniel S Larkin
(74) *Attorney, Agent, or Firm*—Michael K. Boyer

(57) ABSTRACT

A system for detecting fine liquid, e.g., oil, particles in a gas system having a conduit through which a gas, e.g., hydrogen, air, etc., will flow. The detection system includes a monitor including a high sensitivity photometric sensor, a data acquisition unit and flow and pressure control components to control the pressure and rate of flow of the gas to the monitor. The detection system is arranged to detect the presence of fine liquid particles the gas passing through the conduit and to provide an alert signal representative of the mass count of such particles in response thereto.

21 Claims, 2 Drawing Sheets

LIQUID PARTICLE MASS MEASUREMENT IN GAS STREAMS

CROSS-REFERENCE TO RELATED APPLICATIONS

This application is a Continuation-In-Part of U.S. patent application Ser. No. 11/249,206, filed on Oct. 13, 2005, now U.S. Pat. No. 7,343,781, entitled System And Methods For Detecting Liquid Particles In A Gas Stream, whose disclosure is incorporated by reference herein.

BACKGROUND OF THE INVENTION

This invention relates generally to liquid particle/droplet detecting systems, and more particularly to systems for detecting particles or droplets of liquids, e.g., oils, in gas systems making use of at least one gas compressor or other device which may introduce fine particles of such liquid(s) into gas in the system.

As should be appreciated by those skilled in the art, in gas producing, transport and/or storage systems, such as natural gas feed stock systems, fine oil mist may enter into the conduit carrying the natural gas as a result of leakage of oil from seals of compressors. The presence of such minute particles or droplets of oil (sometimes referred to as "oil droplet breakthrough") can contaminate the natural gas. Moreover, oil mist in natural gas feed stock may reduce the efficiency of the hydrogenation catalyst by deactivating it and also causing it to "cake", thereby creating a pressure drop across a hydrogenator/desulfurizer. Thus, it is a common practice to make use of separators, coalescers, adsorbent beds, and filters in gas systems downstream of the high pressure gas compressor (or any other device which may introduce fine oil particles into the gas). Such devices are designed to capture such oil particles and thereby prevent them from contaminating the final gas product. It has also been determined that in aircraft HVAC systems a mist of fine oil particles from some component in the air flow path may find its way into the ventilation system of the pilot's compartment and/or the passenger cabin. Obviously, this occurrence is undesirable.

The patented prior art includes various particle detecting devices that make use of light scattering techniques to detect the presence of particles in fluid streams. For example, in U.S. Pat. Nos. 5,864,399 (Girvin et al.) and 5,642,193 (Girvin et al.) there are disclosed particle detectors, each of which employs a laser disposed in a resonant cavity and an intra-cavity view volume. The resonant cavity is defined by two spaced apart mirrors, with the laser medium positioned between them, defining a light path. A pump source is optically coupled to drive the laser medium to produce coherent light having a first wavelength. The view volume is positioned in the light path, between the first mirror and the laser medium, to introduce particles into the resonant cavity so that light impinging there-upon produces scattered light. A detector is disposed to sense light scattered from the view volume and produces signals proportional to the light sensed. A displaying device, such as a pulse height analyzer, is in electrical communication to receive the signals produced by the detector to quantitatively display the intensity of the light sensed.

DE 10162278 discloses a system of detecting the presence of air compressor produced oil droplets in compressed gas stream by heating and expanding a partial aerosol stream, to thereby transform the droplets into a gas which is subsequently analyzed by a gas sensor.

Devices for detecting particles in a fluid stream are also commercially available. For example, Thermo Andersen, Inc., of Franklin, Mass. sells a HPM-1000 particulate monitor that is designed to be installed directly in line with compressed air/gas streams to provide continuous measurement of oil mist carryover, entrained water mist, and particulate contamination at pressures up to 350 psig. The HPM-1000 monitor uses a high sensitivity nephalometric (photometric) sensor, whose light scattering detection configuration has been optimized for the measurement of fine particle contamination in compressed air and gas streams.

While the aforementioned prior art is generally suitable for its intended purposes, it nevertheless leaves something to be desired from the standpoint of providing a monitoring system and method capable of detecting low levels of fine oil or other liquid particles in a gas stream from any device which may introduce fine oil or other liquid particles into the stream and to alert an operator to that fact. In our patent application Ser. No. 11/249,206 filed on Oct. 13, 2005, now U.S. Pat. No. 7,343,781, from which this application claims priority and which is assigned to the same assignee as this invention there is disclosed and claimed a system that addresses that need to provide an alert signal indicative of the presence of oil or other liquid particles in the gas. The alert signal can be used to institute automatic remedial action, e.g., shut off at least a part of the system and/or bring another part of the system on-line to prevent the further contamination of the gas product.

In particular, our U.S. Pat. No. 7,343,781 discloses a system for detecting fine liquid, e.g., oil, particles in a gas system having a high pressure compressor and at least two gas handling devices, e.g., a coalescer and at least one adsorber. The detection system uses plural sensors and a monitor unit. Each of the monitors is arranged for detecting the presence of fine liquid particles in the gas by means of light scattering and for providing an output signal to a data acquisition unit. The data acquisition unit operates in response to the detection of the fine liquid particles in various portions of the gas system and to provide alert signals in response thereto. The alert signals can be used to control associated valves in the gas system to bring about a desired result.

For some gas carrying systems, e.g., natural gas reformation system, HVAC systems such as in aircraft, clean rooms or other controlled environments in manufacturing facilities etc., the prior art systems as disclosed above may not be suitable, e.g., they may be too complex or expensive. Moreover, in some gas supply systems automated control may not be necessary. The systems and methods of the invention of our U.S. Pat. No. 7,343,781, absent its feed-back or automated control aspects, can be used for such simplified (e.g., non-automatic control) applications. Thus, the subject invention is directed to providing systems and methods to aid in identification of fine oil (or other liquid) particles into a downstream gas supply by monitoring the gas at one point and reacting to any appreciable increase in oil levels to provide a signal indicative of the absolute value of the liquid detected. Moreover, the systems and methods of the subject invention are capable of detecting extremely low levels of liquid particles. Thus, the usage of the systems and methods of this invention enables an early warning of oil/liquid droplet presence that may be an unsafe or unhealthy environment, or indicative of a pump/compressor/fan failure.

The disclosure of the previously identified patents, patent applications and publications is hereby incorporated by reference.

BRIEF SUMMARY OF THE INVENTION

A detection system for detecting the presence of fine liquid particles in a gas system including a compressor or other device which may introduce fine liquid particles into a gas-carrying conduit. The detection system comprises a first monitor, a data acquisition unit and pressure and flow control means. The first monitor is arranged for detecting the presence of fine liquid, e.g., oil, particles in the gas by means of light scattering and for providing an output signal to the data acquisition unit in response to the detection of such fine liquid particles. The first monitor is in communication with the interior of the first gas-carrying conduit. The pressure and flow control means is arranged to control the pressure and flow rate of the gas in the gas-carrying conduit at the first monitor so that it is within a predetermined range, whereupon the data acquisition unit provides at least one output signal indicative of an absolute value change in the mass count of any fine liquid particles in the gas carrying conduit.

In accordance with another aspect of this invention there is provided a method for detecting the presence of fine liquid particles in a gas system, e.g., a natural gas system or an aircraft ventilation system, the gas system comprising a compressor or other device which may introduce fine liquid particles into a gas-carrying conduit. The detection system comprises a first monitor, a data acquisition unit and pressure and flow control means. The first monitor is arranged for detecting the presence of fine liquid particles in the gas by means of light scattering and for providing an output signal to the data acquisition unit in response to the detection of such fine liquid particles. The method comprises coupling the first monitor in communication with the interior of the first gas-carrying conduit, operating the pressure and flow control means to control the pressure and flow rate of the gas in the gas-carrying conduit at the first monitor, whereupon the pressure and flow rate of the gas in the gas-carrying conduit is within a predetermined range, and operating said data acquisition unit to provide at least one output signal indicative of an absolute value change in the mass count of any fine liquid particles in the gas carrying conduit.

In accordance with another aspect of this invention the pressure and flow control means is adjustable in automatic response to a signal from the data acquisition unit, e.g., the pressure and flow control means is arranged to control the flow within a range of approximately +/−2% for rates in the range of approximately one to thirty liters per minute, and to control the pressure within a range of +/−10 PSIG for pressures in the range of approximately 100 to 350 PSIG and approximately +/−5% of the value in the range 1 to 100 PSIG.

DETAILED DESCRIPTION OF THE INVENTION

Figure 1:
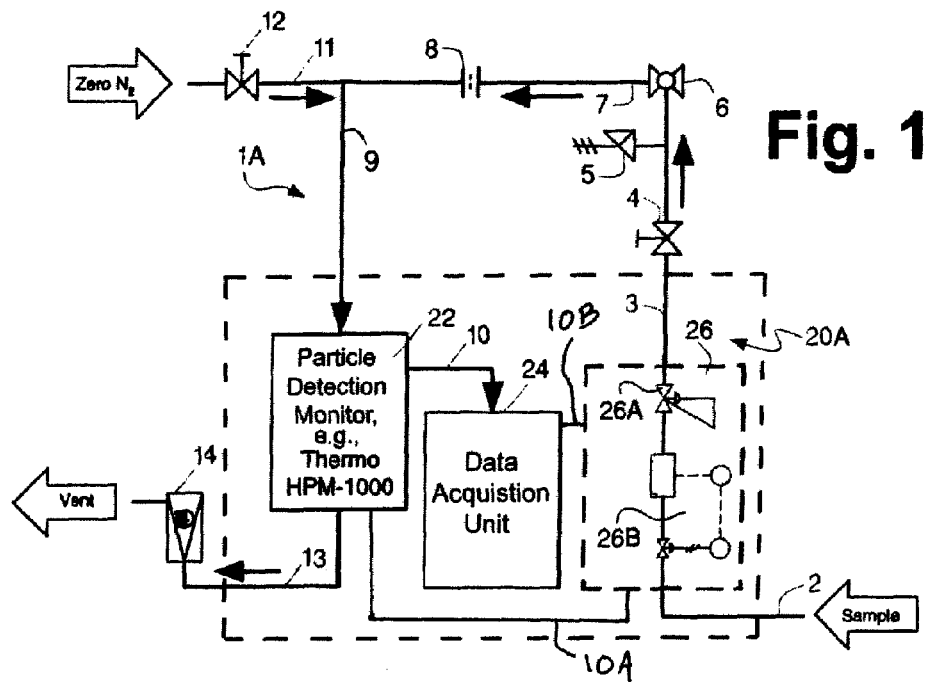
FIG. 1 is a schematic view of one exemplary embodiment of the detection system of the subject invention shown in an exemplary embodiment of a conventional gas system, e.g., a non-flammable gas system.
Figure 2:
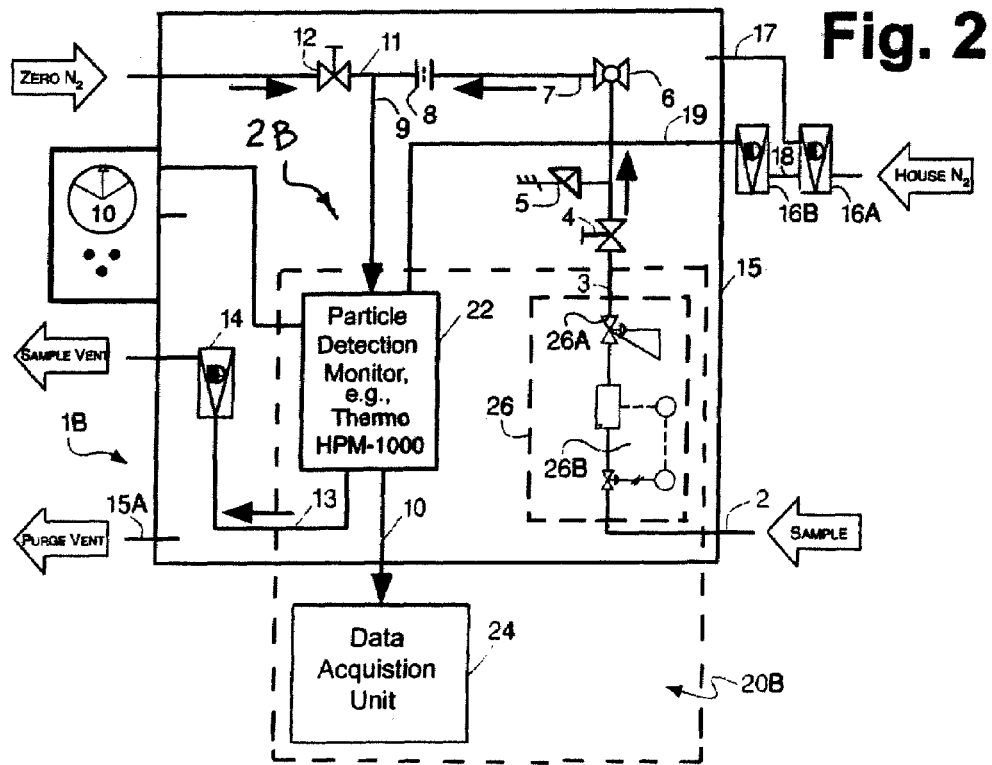
FIG. 2 is a schematic view of the embodiment of the detection system shown in FIG. 1 configured for use in another exemplary embodiment of a conventional gas system, e.g., a flammable gas system.
Figure 3:
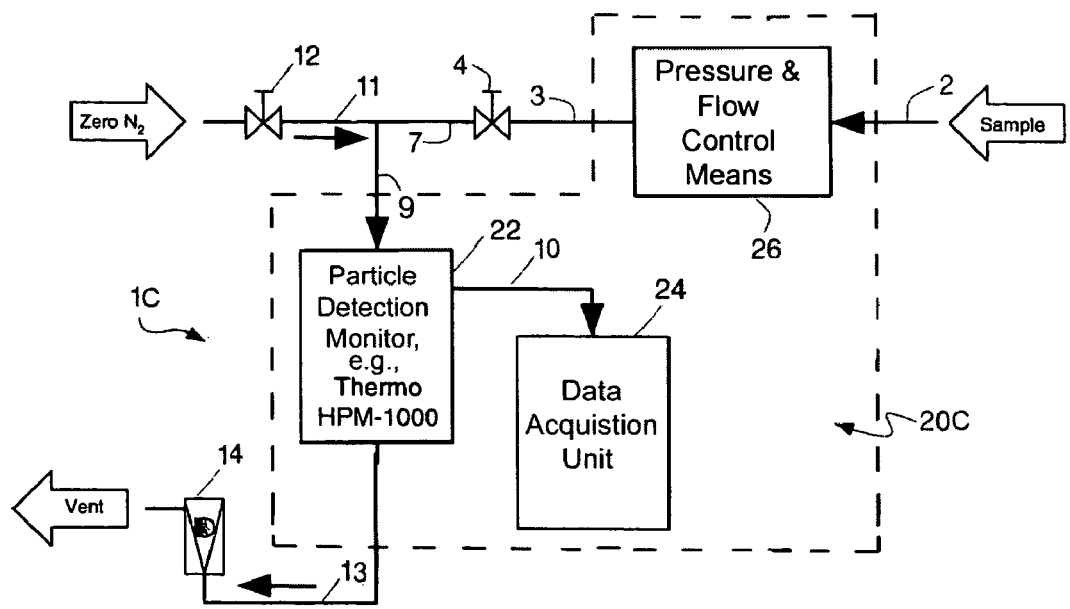
FIG. 3 is a schematic view of the embodiment of the detection system shown in FIG. 1 configured for use in another exemplary embodiment of a gas system, in this case a HVAC or other ventilation system, such as may be found in an aircraft, in an enclosed environment manufacturing facility, etc.

Referring now to the various figures of the drawing wherein like reference numbers refer to like parts, there is shown in FIGS. 1, 2 and 3 exemplary embodiments of fine liquid particle/droplet detection system 20A, 20B and 20C, respectively, which are constructed in accordance with this invention for use with various types of systems for through which a gas will pass. As will be described in considerable detail later each of the systems 20A, 20B and 20C comprises a single particulate detection monitor 22, an associated data acquisition unit 24 and pressure and flow control means 26. The details and operation of those components will be described later and are consistent with that described in our aforementioned U.S. Pat. No. 7,343,781.

Before describing the fine liquid particle/droplet detection systems of this invention it should be pointed out that such system are useful in any gas system, like the systems of FIGS. 1-3 or any other systems wherein oil or other fine liquid particles, e.g., hydrocarbon compounds, fluorocarbon compounds, silicone or halocarbon based lubricants, coolants and other materials which condense at the temperature and pressure of operation of the system, may gain egress into gas flowing through some passageway or conduit (e.g., be drawn in the gas flow by a venturi effect). Thus, the subject invention is not limited to systems including a high pressure compressor. Rather, this invention can be used in any systems including components, e.g., lubricated valves, fittings, etc., including a grease, oil, other lubricants, coolants, etc. which may be enable any type of liquid to be drawn into (or otherwise introduced) a gas stream. The gas stream may be an elemental gas (such as hydrogen, etc.), combined elemental gases (such as silane ($SiH_4$), $CO_2$, etc.), a hydrocarbon gas (such as methane, propane, butane, etc.), a halohydrocarbon gas (such as SUVA® gases containing either fluorine or chlorine, etc.) or mixtures of gases (such as air). One typical application is the reformation of methane into carbon monoxide and hydrogen. For various applications, e.g., in the metals processing industry, such as the manufacture of the highest quality stainless steel, ultra-pure hydrogen is required. The presence of even minute amounts of oil or other liquid particles in the hydrogen may result in an inferior product. Thus, such industries frequently demand that the hydrogen have as low a hydrocarbon content as possible. The subject invention can be used to achieve that end.

The gas system 1A (FIG. 1) in which the detection system 20A is used comprises a gas supply system carrying a non-flammable gas. In FIG. 2 the gas supply system 2B in which the detection system 20B is used comprises a gas supply system making use of a flammable gas. In FIG. 3 the system 1C in which the detection system 20C is used comprises an HVAC system or any other system carrying air, e.g., a ventilation system to the interior of an aircraft, a clean room or other controlled environment. It must be pointed out at this juncture that the systems 1A, 1B and 1C are merely exemplary of many types of gas systems making use of at least one high pressure gas compressor or other device which may introduce fine oil particles into a gas stream. Again it must be reiterated that, while the subject detection systems of this invention will be described for detecting fine particles of oil, that too is merely exemplary, since the detection systems of this invention and the methods of this invention can be used for detecting the presence in a gas stream of any type of liquid particles which may tend to leak or be accidentally introduced into the gas stream, and for indicating that occurrence and providing a signal indicative of the absolute value thereof.

Before describing the detection system 20A, a brief description of the exemplary gas system 1A is in order. In this exemplary embodiment the gas system 1A receives the gas to be monitored (the gas is identified by the legend "Sample" within the arrow shown in FIG. 1) from a conduit 2 carrying that gas. Located upstream of the conduit is any device or component (not shown) that may introduce fine liquid particles or droplets as a mist into the gas stream. The pressure and flow control means 26 is connected in the conduit 2 and its output is provided via a conduit 3. Downstream of the pressure and flow control means 26 is a manual shut-off (on/off) valve 4 in the conduit 3. A safety pressure relief valve 5 is located in the conduit 3 downstream of the valve 4. An optional isolation valve 6 is located in the conduit 3 downstream of the relief valve 5. The output of the valve 6 is provided via a conduit 7. A restrictor, e.g., needle valve, 8 is located in the conduit 7. The conduit 7 is connected to a conduit 9 which serves as the input to the particulate detection monitor 22 of the fine liquid particle/droplet detection system 20A. Thus, the conduit 9 serves to carry the gas to be sampled for liquid particulates (i.e., the "Sample" gas) to the monitor 22. As will be described in detail later, the monitor 22 is arranged to provide electrical output signals indicative of the level of oil or other liquid particles in the gas in the conduit 9 to the data acquisition unit 24 via an electrical line 10.

In order to calibrate the monitor 22 and to purge it of any residual contaminants before it is used to detect the presence of particulates in the Sample gas stream, the system 1A includes another input to the monitor. That input is provided via a conduit 11 and serves to carry a purge gas, e.g., nitrogen (designated by the legend "Zero $N_2$" within the arrow shown in FIG. 1) from a gas source (not shown). The purge gas input conduit 11 merges with the sample gas conduit 7 as a joint input into the conduit 9 leading to the monitor 22. A manual shut off valve 12 is connected in the purge gas input line 11 between the source of the purge gas and conduit 9. The gas output of the monitor 22 is provided by a conduit 13 to vent the gas to some means (not shown and designated by the legend "Vent" within the arrow shown in FIG. 1). A flow meter 14 (whose function and operation will be described later) is located in the conduit 13 between the monitor and the vent.

In the use of medical gases, e.g., oxygen or other breathing gas mixtures, for patients who must be housed in a chamber or other closed environment, the gases may be compressed using halocarbon oil lubed equipment. In some cases oil-less compressors/pumps are used. Hence, the subject invention has application for use in medical gas monitoring systems, e.g. in-home care, hospitals, nursing homes and clinics.

The purging of the monitor 22 of any residual contaminants, e.g., oil droplets, residual gas, etc., is accomplished by closing the manual shut off valve 4, thereby preventing any of the Sample gas from gaining access to the monitor via conduit 9. Once that has been accomplished the manual shut off valve 12 can then be opened to introduce a purge gas, e.g., nitrogen, via communicating conduits 11 and 9 into the monitor 22. Before introducing the purge gas into the system, the optional valve 6 may be closed, to thereby prevent the purge gas from flowing upstream, in case the valve 4 was not shut. The introduction of the purge gas into the system so that it flows through the monitor 22 has the effect of flushing any contaminants out of the monitor via output conduit 13 and flow valve 14 to the vent. The meter 12 is arranged to be adjusted so that the rate of flow of the purge gas through the monitor can be made consistent with the rate of flow of the Sample gas through the monitor 22, e.g., twenty-five liters/minute, thereby ensuring accurate calibration of the monitor. To that end the presence of the flow meter 14 in the output conduit 13 enables one to readily adjust the flow rate of the purge gas to the desired level. After the system 20A has been purged, it can be calibrated to a zero level. Once this has been accomplished the detection system 20A is ready for use with the Sample gas to detect the presence and absolute value of any liquid particles therein.

As mentioned above, the detection system 20A comprises a single particulate detection monitor 22, the data acquisition unit 24 and the pressure and flow control means 26. The monitor 22 makes use of a high sensitivity nephalometric (photometric) sensor and is connected to the data acquisition unit via line 10. The data acquisition unit may be any conventional device, such as data logger, a computer or a portion of a distributed control system (DCS) of the facility operating the system 1A. One particularly suitable commercially available monitor 22 is the above mentioned HPM-1000 particulate monitor of Thermo Andersen, Inc. As mentioned above, this monitor and its associated sensor is designed to measure the concentration of gas borne particulate matter (liquid or solid), at pressures up to 350 psig. The high sensitivity nephalometric (photometric) sensors' light scattering detection configuration of this invention is optimized for the measurement of fine particle contamination in compressed air and gas streams. Thus, the system 20A is designed to work within the following parameters: Sample Pressures: 0 psig-350 psig. Sample Flow Rates: 1 L/min-30 L/min. Sensor Electrical Requirements: 90-265 VAC, 50-60 Hz. Measurement Range: 0.01 mg/m3 to 400 mg/m3 or 0.03 ug/ft3 to 11,330 ug/ft3. It should be pointed out at this juncture that other oil or other liquid particle monitors can be used in lieu of the HPM-1000 monitor.

Figure 1A:
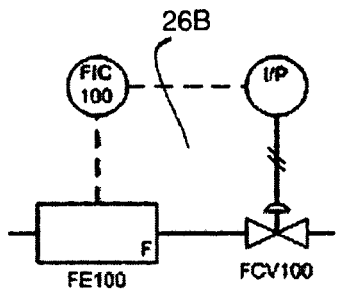
FIG. 1A is a schematic diagram of one exemplary portion of the exemplary flow and pressure control means used in the system of FIG. 1.

The HPM-1000 high pressure particulate monitor is specified by its manufacturer as being capable of measurement and calibration independent of flow rate. However, it has been discovered that enhanced effective and accurate usage, the flow rate and pressure be controlled. Thus, in the exemplary embodiment disclosed herein the input to the HPM1-1000 the monitor 22 is via the pressure and flow control means 26. That means comprises any commercially available devices, such as a pressure control valve 26A and a flow control valve and associated components collectively designated by the reference number 26B and shown in more detail in FIG. 1A. Such devices are available from Swagelock Company of Solon, Ohio, Parker Hannifin Corporation of Cleveland, Ohio and others. The valves 26A and 26B are connected in series between the monitor 22 and the line, conduit or device carrying the sample gas. The valves may be adjusted manually or under automated control via electrical line 10A from a data logger (not shown) or any other associated equipment. Each of the pressure and flow control means is arranged to control the flow within a range of approximately +/−2% for rates in the range of approximately one to thirty liters per minute, and to control the pressure within a range of +/−10 psig for pressures in the range of approximately 100 to 350 psig and approximately +/−5% of the value in the range of approximately 1 to 100 psig. As will be appreciated by those skilled in the art the settings for the pressure and flow are dependent upon the conditions of the system 1A, 1B, 1C in which the subject invention is to be used. Thus, the pressure and flow rate of the system 1A at the location where the monitor 22 is to be located should be determined and the appropriate setting of pressure and flow made consistent therewith. Also, it is desirable to set the pressure as low as possible and consistent with the make-up of the system 1A to prevent the liquid particles/droplets from condensing out of the gas and onto the conduit, tubing or device(s) in which the gas passes. One exemplary setting for the pressure and flow could be a pressure of approximately 15 psi at a flow rate of approximately twenty-five liters/minute. It has been determined that particle size for detection by the specific embodiment of the monitor 22 disclosed above can be in the range of 0.1 to 10 microns (e.g., or any other effective range for the monitor). However, particles in the range of one to one-hundred microns can also be detected by the subject invention, depending upon ambient conditions, e.g., temperature since it may affect condensation.

The data acquisition unit 24, be it a data logger, a computer, a portion of a DCS or some other device, is arranged to receive signals from the monitor 22, to analyze those signals and to provide alert signals indicative of the absolute level of liquid particles detected. This signal may be used for various functions, e.g., to repair or replace any equipment/component found to be the source of the introduced liquid particles, etc. By so doing the gas system 1A can be maintained in a condition wherein the level of oil or other liquid particle/droplets is below a desired threshold level. As discussed in our U.S. Pat. No. 7,343,781, if higher than normal levels of oil or other liquid contaminant particles are detected, the system can be arranged to take automated corrective action (e.g., switch an associated valve to send gas feed to a device or component for trapping it, e.g., to another filter bed or coalescer to prevent the oil or other liquid contaminant being passed into the final product). Thus, the data acquisition unit 24 may include one or more output lines for automatically controlling the operation of any appropriate valves in the gas system 1A to take any component out of the system and/or connect any component into the system to thereby ensure that the system can continue to operate at a desired level of gas purity.

As also discussed in our U.S. Pat. No. 7,343,781, if there is a relatively high concentration of liquid particles/droplets in the gas, such an occurrence can result in the condensation of the liquid on the side of the tubing carrying the gas, whereupon there will be a precipitous drop in the particles/droplets detected by the monitor. Accordingly, the detection of a precipitous drop in particles/droplets detected can be used by the data acquisition unit 24 to provide appropriate warning (alert) signals to operating personnel (or control signals to take automated corrective action, if such is desired).

For some applications wherein the monitor 22 will be subjected to substantial vibration, e.g., a monitor mounted on or near a particular vibration prone component, e.g., a high pressure compressor, it may be desirable to make use of conventional vibration isolator to ensure proper monitor operation. One particularly suitable isolator for that purpose is the 6M MICRO/LEVEL® Elastomer Isolator available from VIBRO/DYNAMICS Corporation of Broadview, Ill.

Operation of the system 20A in the gas system 1A to detect the presence of liquid particles in the Sample gas is as follows. The shut off valve 12 is closed to prevent any additional purging gas from gaining ingress to the monitor, whereupon any residual purging gas in the monitor may flow out to the vent. The Sample gas can then be introduced into the system by opening the shut off valve 4. The pressure and flow rate of the Sample gas through the conduit 2 is adjusted by the pressure and flow control means 26, e.g., its components 26A and 26B, in the same manner as described above and in our U.S. Pat. No. 7,343,781. Since the monitor 22 is arranged to operate up to pressures up to about 350 psig and since the pressure of the Sample gas introduced into conduit 3 may greatly exceed that value (such as could occur by virtue of a failure in the pressure and control means 26), the pressure relief valve 5 is set at approximately level, e.g., 350 psig, thereby protecting the system. The Sample gas at the controlled pressure and flow rate then passes through the optional valve 6 and its associated conduit 7, through the restrictor 8 to the monitor input conduit 9. The restrictor 8 is arranged to prevent backflow of the purge (zero) gas, e.g., nitrogen into the sample line. The Sample gas then passes into the monitor 22 wherein the presence of any liquid particles is detected and the absolute value of the mass count of such particles is determined and provided as an electrical output signal on line 10 to the data acquisition unit. The pressure and control means 26 is arranged to be adjusted in response to a signal provided via electrical line 10B from the data acquisition unit. The pressure and control means 26 can be arranged to be adjusted in automatic response to the signal from the data acquisition unit.

In FIG. 2 there is shown an alternative gas system 1B making use of a detection system 20B constructed in accordance with this invention. The gas system 1B represents any flammable gas system, e.g., a system for reforming natural gas into hydrogen. In the interest of brevity the common components of the gas systems 1A and 1B and of the detection systems 20A and 20B will be given the same reference numbers and the details of their construction, arrangement and operation will not be reiterated. Since the system 1B will be used with a flammable gas, the detection system 20B (with the exception of the data acquisition unit 24) and most of the components of the gas system 1B are housed within a fire/explosion proof/resistant housing or enclosure 15. If desired the data acquisition unit 24 can also be located within the enclosure. The housing or enclosure 15 includes a portion containing a meter M. The meter M provides the user of the system with direct knowledge of the volume flow of purge gas passing in/out of the housing to assure safe operation. This is usually ten times the volume of the enclosure in liters of purge gas per hour.

Since the system 1B entails use of a flammable gas, the interior of the housing 15 is arranged to be purged of any potentially explosive gases or liquids. This is accomplished by the introduction of a purge gas, e.g., nitrogen, therein. Moreover, since the interior of the monitor itself may be the repository of some residual explosive gas or liquid, the monitor's interior is also arranged to be purged of any such gases or liquids by the introduction of the purge gas therein. To that end the subject invention makes use purge gas e.g., nitrogen (designated by the legend "House $N_2$" within the arrow shown in FIG. 2), although other non-flammable gases may be used for this purpose. The purge gas is provided from a gas source (not shown) into a first flowmeter 16A (referred to as the enclosure or cabinet flowmeter). The outlet of the enclosure flowmeter 16A is connected to a conduit 17 which is in fluid communication with the interior of the enclosure 15. Another flowmeter 16B (referred to as the instrument flowmeter) is also provided and is connected to a conduit 18, which is connected downstream of the enclosure flowmeter 16A. The outlet of the instrument flowmeter 16B is connected to a conduit 19 which is in fluid communication with the interior of the monitor 22. The purge gas introduced into the enclosure 15, vents from the enclosure via a purge vent aperture 15A. The purge gas introduced into the monitor vents from the monitor via conduit 13, flowmeter 14 and an associated vent (identified by the legend "Sample vent" within the arrow in FIG. 2) which extends out of the enclosure 15. It is through the Sample vent that the Sample gas monitored by the system 20B is also vented. Thus, since the Sample gas is in this embodiment is flammable, some means (not shown) is typically provided coupled to the Sample vent for collecting the sample gas to ensure that it is collected and/or stored in a safe condition.

The operation of the system 20B to detect oil/liquid particles in the Sample gas is as described heretofore with respect to the systems 1A and 20A.

As mentioned earlier, the subject invention can be utilized in ventilating systems for providing air to some enclosed structure, e.g., the interior of an aircraft, a clean room or other environmentally controlled room in a manufacturing facility, etc. In FIG. 3 there is shown a detection system 20C in an exemplary aircraft HVAC system. As is known, in an aircraft system HVAC system various oil or other liquid contaminant particles can gain ingress into the passenger cabin and/or pilot compartment via the ventilation ducts forming a part of the HVAC system. Such action may occur through breakdown of seals in various components of the HVAC system. If this occurs it is of considerable importance that one can accurately determine the amount of particles introduced into the air stream to either the pilot's compartment or passenger cabin.

As best seen in FIG. 3, the detection system 20C is similar in construction to the system 20A and 20. Thus, in the interest of brevity the common components of the detection system 20C will be given the same reference numbers as the systems 20A and 20B. Moreover, the details of the construction, arrangement and operation of its components will not be reiterated. The gas system 1C in which the detection system 20C is used comprises a source of gas to be sampled. In this case it comprises air from the aircraft's HVAC system and is taken off any conduit, passageway or duct through which air is brought to the pilot's compartment and the passenger's cabin. The air, identified by the legend "Sample" within the arrow in FIG. 3, is introduced into the conduit 2 of the system 1C. The outlet of the pressure and flow control means 26 is provided via conduit 3. The shut-off valve 4 is located in the conduit 3 and its output is provided by the conduit 7. The conduit 7 merges and is in fluid communication with the conduit 9 leading to the monitor 22. The electrical output of the monitor is provided via line 10 to the data acquisition unit 24. Purge gas (designated by the legend "Zero $N_2$" within the arrow shown in FIG. 3) is arranged to pass through shut-off valve 12 when it is opened, whereupon the purge gas flows into communicating conduit 11 and from there merges into conduit 9 to the monitor 22. The gas outlet of the monitor is provided via conduit 13 and flowmeter 14 leading to the vent.

It should be pointed out at this juncture that the "Zero $N_2$" gas portion of the system 1C when used in mobile applications, e.g., aircraft, need not be required to stay with the system after its initial use. Rather, once that gas has been used, the valve 12 can be closed and then the gas source can be detached and removed from the system. Therefore, there is no need to carry the Zero $N_2$ gas supply on the aircraft (or in any other mobile unit in which the subject invention is utilized).

The operation of the system 20C to detect oil/liquid particles in the Sample gas is as described heretofore with respect to the systems 20A and 20B. When the system 20C is used in aircraft applications the signals from the data acquisition unit which are indicative of the presence of oil or other liquid particles in the air system can be wirelessly transmitted from the aircraft to the ground. Thus, after the aircraft has landed appropriate restorative measures can be taken, e.g., servicing the offending component(s). If it is desired to effect restorative measures in automatic response to the detection of the oil/liquid particles, e.g., while the aircraft is flying, the aircraft's HVAC system can be constructed and arranged with appropriate valves and other components that can be automatically connected into or out of the system to achieve that end. Such automatic control in such a case would be in accordance with the teachings of our U.S. Pat. No. 7,343,781.

While the invention has been described in detail and with reference to several specific examples thereof, it will be apparent to one skilled in the art that various changes and modifications can be made therein without departing from the spirit and scope thereof.

What is claimed is:

1. A detection system for detecting the presence of fine liquid particles in a gas system, the gas system comprising fine liquid particles in a gas-carrying conduit, said detection system comprising a first monitor, a data acquisition unit and pressure and flow control means, said first monitor being arranged for detecting the presence of fine liquid particles in a gas by means of light scattering and for providing an output signal to said data acquisition unit in response to the detection of such fine liquid particles, said first monitor being in communication with the interior of the gas-carrying conduit, said pressure and flow control means being arranged to control the pressure and flow rate of the gas in the gas-carrying conduit so that the pressure and flow rate at said first monitor is within a predetermined range, whereupon said data acquisition unit provides at least one output signal indicative of an absolute value change in the mass count of any fine liquid particles in the gas carrying conduit; wherein said pressure and flow control means is arranged to control the flow within a range of about +/−2% for rates in the range of about one to thirty liters per minute, and to control the pressure within a range of +/−10 psig for pressures in the range of about 100 to about 350 psig and about +/−5% of the value in the range about 1 to about 100 psig.

2. The detection system of claim 1 wherein said pressure and flow control means is adjustable.

3. The detection system of claim 2 wherein said pressure and flow control means is arranged to be adjusted in response to a signal from said data acquisition unit.

4. The detection system of claim 3 wherein said pressure and flow control means is arranged to be adjusted in automatic response to said signal from said data acquisition unit.

5. The detection system of claim 1 wherein the gas comprises at least one member selected from the group consisting of elemental gases, hydrocarbon gases, halohydrocarbon gases, combined elemental gases and mixtures of any of the foregoing gases, and wherein said liquid particles comprise one or more liquids in the group consisting of hydrocarbon compounds, fluorocarbon compounds, silicone based lubricants, coolants, and materials that condense at the temperature and pressure of operation, and wherein said monitor is arranged for detecting the presence of such fine particles in said gas.

6. The detection system of claim 5 wherein said particles are in the size range of about 0.1 to about 10 microns.

7. The detection system of claim 1 wherein said particles are in the size range of about 1 to about 100 microns.

8. The detection system of claim 1 wherein said particles are in the size range of about 0.1 to about 10 microns.

9. The detection system of claim 1 wherein said gas system comprises an HVAC system for a controlled environment and wherein said gas comprises air.

10. A method for detecting the presence of fine liquid particles in a gas system, the gas system comprising fine liquid particles in a gas-carrying conduit, said detection system comprising a first monitor, a data acquisition unit and pressure and flow control means, said first monitor being arranged for detecting the presence of fine liquid particles in a gas by means of light scattering and for providing an output signal to said data acquisition unit in response to the detection of such fine liquid particles, said method comprising:
- (A) coupling a first monitor in communication with the interior of the first gas-carrying conduit,
- (B) operating said pressure and flow control means to control the pressure and flow rate of the gas in the gas-carrying conduit at said first monitor, whereupon said pressure and flow rate in the gas carrying conduit at said first monitor is within a predetermined range, and
- (C) operating said data acquisition unit to provide at least one output signal indicative of an absolute value change in the mass count of any fine liquid particles in the gas carrying conduit, wherein said gas system comprises an HVAC system for a controlled environment and said gas comprises air.

11. The method of claim 10 additionally comprising:
- (D) adjusting the pressure and flow control means.

12. The method of claim 11 wherein said adjustment of the pressure and flow control means is in response to a signal from said data acquisition unit.

13. The method of claim 12 wherein said adjustment of the pressure and flow control means is in automatic response to said signal from said data acquisition unit.

14. The method of claim 10 wherein said pressure and flow control means is operated to control the flow within a range of about +/−2% for rates in the range of about one to thirty liters per minute, and to control the pressure within a range of +/−10 PSIG for pressures in the range of about 100 to about 350 psig and about +/−5% of the value in the range about 1 to about 100 psig.

15. The method of claim 10 wherein the gas comprises one or more gases in the group consisting of elemental gases, hydrocarbon gases, halohydrocarbon gases, combined elemental gases and mixtures of any of the foregoing gases, and wherein said liquid particles comprise one or more liquids in the group consisting of hydrocarbon compounds, fluorocarbon compounds, silicone based lubricants, coolants, and materials that condense at the temperature and pressure of operation, and wherein said monitor is arranged for detecting the presence of such fine particles in said gas.

16. The method of claim 15 wherein said particles are in the size range of about 0.1 to about 10 microns.

17. The method of claim 10 wherein said particles are in the size range of about 1 to about 100 microns.

18. The method of claim 10 wherein said particles are in the size range of about 0.1 to about 10 microns.

19. The method of claim 10 wherein said HVAC system is in an aircraft.

20. A method for detecting the presence of fine liquid particles in a gas system, said gas system comprising a first monitor, a data acquisition unit and pressure and flow control means, said first monitor being arranged for detecting the presence of fine liquid particles in a gas by means of light scattering and for providing an output signal to said data acquisition unit in response to the detection of such fine liquid particles, said method comprising:
- (A) coupling a first monitor in communication with the interior of the first gas-carrying conduit,
- (B) operating said pressure and flow control means to control the pressure and flow rate of the gas in the gas-carrying conduit at said first monitor, whereupon said pressure and flow rate in the gas carrying conduit at said first monitor is within a predetermined range, and
- (C) operating said data acquisition unit to provide at least one output signal indicative of an absolute value change in the mass count of any fine liquid particles in the gas carrying conduit; wherein said pressure and flow control means is operated to control the flow within a range of about +/−2% for rates in the range of about one to thirty liters per minute, and to control the pressure within a range of +/−10 PSIG for pressures in the range of about 100 to about 350 psig and about +/−5% of the value in the range about 1 to about 100 psig.

21. A method for detecting the presence of fine liquid particles in a gas system, said gas system comprising a first monitor, a data acquisition unit and pressure and flow control means, said first monitor being arranged for detecting the presence of fine liquid particles in a gas by means of light scattering and for providing an output signal to said data acquisition unit in response to the detection of such fine liquid particles, said method comprising:
- (A) coupling a first monitor in communication with the interior of the first gas-carrying conduit,
- (B) operating said pressure and flow control means to control the pressure and flow rate of the gas in the gas-carrying conduit at said first monitor, whereupon said pressure and flow rate in the gas carrying conduit at said first monitor is within a predetermined range, and
- (C) operating said data acquisition unit to provide at least one output signal indicative of an absolute value change in the mass count of any fine liquid particles in the gas carrying conduit; wherein the gas system comprises at least one member selected from the group consisting of natural gas, natural gas reformation system, and hydrogen.

\* \* \* \* \*